(12) United States Patent
Beard et al.

(10) Patent No.: US 6,597,170 B1
(45) Date of Patent: Jul. 22, 2003

(54) OPTIMAL EXCITATION PULSE SHAPING FOR MULTI-FREQUENCY MEASUREMENTS IN NMR LOGGING

(75) Inventors: David Beard, Houston, TX (US); Gregory Itskovich, Houston, TX (US); Arcady Reiderman, Houston, TX (US); Songhua Chen, Katy, TX (US)

(73) Assignee: Baker Hughes Incorporated, Houston, TX (US)

( * ) Notice: Subject to any disclaimer, the term of this patent is extended or adjusted under 35 U.S.C. 154(b) by 60 days.

(21) Appl. No.: 09/606,998

(22) Filed: Jun. 29, 2000

(51) Int. Cl.⁷ .................................................. G01V 3/00
(52) U.S. Cl. ............................................................ 324/303
(58) Field of Search ................................. 324/303, 307, 324/309, 314, 318

(56) References Cited

U.S. PATENT DOCUMENTS

| | | | |
|---|---|---|---|
| 4,320,399 A | 3/1982 | Buck et al. ............ 343/17.1 R |
| 4,521,733 A | * 6/1985 | Bottomley et al. ......... 324/309 |
| 5,023,551 A | 6/1991 | Kleinberg et al. ........... 324/303 |
| 5,253,270 A | 10/1993 | Petit .............................. 375/43 |
| 5,315,249 A | * 5/1994 | Le Roux et al. ............. 324/309 |
| 5,491,727 A | 2/1996 | Petit ............................ 375/358 |
| 5,619,138 A | * 4/1997 | Rourke ........................ 324/309 |
| 5,936,405 A | 8/1999 | Prammer et al. ........... 324/303 |
| 6,049,205 A | 4/2000 | Taicher et al. .............. 324/303 |

* cited by examiner

Primary Examiner—Edward Lefkowitz
Assistant Examiner—Tiffany A. Fetzner
(74) Attorney, Agent, or Firm—Madan, Mossman & Sriram, P.C.

(57) ABSTRACT

Pulse shaping is used for reducing the interference between echo trains of multiple frequency NMR logging applications in a gradient logging tool. The major contribution to the interference between different logging sequences comes from the sidelobes in the spectra of the excitation signal caused by modulating the RF signal with a square pulse. By shaping the tipping pulse in a CPMG pulse sequence, the interference between logging sequences at proximate frequencies is reduced. The shaped pulse may be a smooth function such as the Chebyshev function or it may be a composite of two rectangular pulses. In an alternate embodiment of the invention, the refocusing pulses are also shaped.

17 Claims, 4 Drawing Sheets

OPTIMAL EXCITATION PULSE SHAPING FOR MULTI-FREQUENCY MEASUREMENTS IN NMR LOGGING

FIELD OF THE INVENTION

The invention is in the field of determination of petrophysical properties of subsurface formations using data from a Nuclear Magnetic Resonance (NMR) tool. Specifically, the invention relates to the use of shaped pulses for reducing interference of signals from different regions of the subsurface in a gradient NMR tool using multiple frequency measurements.

BACKGROUND OF THE INVENTION

A variety of techniques have been utilized in determining the presence and in estimating quantities of hydrocarbons (oil and gas) in earth formations. These methods are designed to determine formation parameters, including among other things, porosity, fluid content, and permeability of the rock formation surrounding the wellbore drilled for recovering hydrocarbons. Typically, the tools designed to provide the desired information are used to log the wellbore. Much of the logging is done after the well bores have been drilled. More recently, wellbores have been logged while drilling of the wellbores, which is referred to as measurement-while-drilling ("MWD") or logging-while-drilling ("LWD"). Measurements have also been made when tripping a drillstring out of a wellbore: this is called measurement-while-tripping ("MWT").

One recently evolving technique involves utilizing Nuclear Magnetic Resonance (NMR) logging tools and methods for determining, among other things porosity, hydrocarbon saturation and permeability of the rock formations. The NMR logging tools are utilized to excite the nuclei of the fluids in the geological formations in the vicinity of the wellbore so that certain parameters such as spin density, longitudinal relaxation time (generally referred to in the art as "$T_1$"), and transverse relaxation time (generally referred to as "$T_2$") of the geological formations can be estimated. From such measurements, porosity, permeability, and hydrocarbon saturation are determined, which provides valuable information about the make-up of the geological formations and the amount of extractable hydrocarbons.

A typical NMR tool generates a static magnetic field $B_0$ in the vicinity of the wellbore, and an oscillating field $B_1$ in a direction perpendicular to $B_0$. This oscillating field is usually applied in the form of short duration pulses. The purpose of the $B_0$ field is to polarize the magnetic moments of nuclei parallel to the static field and the purpose of the $B_1$ field is to rotate the magnetic moments by an angle $\theta$ controlled by the width $t_p$ and the amplitude $B_1$ of the oscillating pulse. With the variation of the number of pulses, pulse duration, and pulse intervals, various pulse sequences can be designed to manipulate the magnetic moment, so that different aspects of the NMR properties can be obtained. For NMR logging, the most common sequence is the Carr-Purcell-Meiboom-Gill ("CPMG") sequence that can be expressed as $$TW-90-(t-180-t-echo)_n \quad (1)$$

where TW is a wait time, 90 is a 90 degree tipping pulse, 180 and is a 180 degree refocusing pulse.

After being tipped by 90°, the magnetic moment precesses around the static field at a particular frequency known as the Larmor frequency $\omega_0$, given by $\omega_0=\gamma B_0$, where $B_0$ is the field strength of the static magnetic field and $\gamma$ is the gyromagnetic ratio. At the same time, the magnetic moments return to the equilibrium direction (i.e., aligned with the static field) according to a decay time known as the "spin-lattice relaxation time" or $T_1$. Inhomogeneities of the $B_0$ field result in dephasing of the magnetic moments and to remedy this, a 180° pulse is included in the sequence to refocus the magnetic moments. This gives a sequence of n echo signals.

U.S. Pat. No. 5,023,551 issued to Kleinberg discloses an NMR pulse sequence that has an NMR pulse sequence for use in the borehole environment which combines a modified inversion recovery (FIR) pulse sequence with a series of more than two, and typically hundreds, of CPMG pulses according to $$[W_i-180-TW_i-90-(\tau-180-\tau-echo)_j]_i \quad (2)$$

where 90 is a 90 degree tipping pulse, 180 is a 180 degree refocusing pulse, $j=-1,2,\ldots J$ and J is the number of echoes collected in a single Carr-Purcell-Meiboom-Gill (CPMG) sequence, where $i=1,\ldots I$ and I is the number of waiting times used in the pulse sequence, where $W_i$ are the recovery times, $TW_i$ are the wait times before a CPMG sequence, and where $\tau$ is the spacing between the alternating 180° pulses and the echo signals. Although a conceptually valid approach for obtaining $T_1$ information, this method is extremely difficult to implement in wireline, MWD, LWD or MWT applications because of the long wait time that is required to acquire data with the different TWS.

There is an inherent inefficiency associated with the tipping and refocusing pulses in the CPMG sequence. The 90° tipping pulse used to modulate the RF signal has a duration one half of the duration of the 180° refocusing pulse, and, as would be known to those versed in the art, the shorter duration pulse has a large bandwidth than the longer duration refocusing pulse. Accordingly, only a portion of the pulses that are tipped will be refocused by the refocusing pulse.

In the typical NMR well logging procedure only about 5 to 10 percent of the total amount of time in between each NMR measurement set is used for RF power transmission of the CPMG pulse sequence. The remaining 90 to 95 percent of the time is used for repolarizing the earth formations along the static magnetic field. Further, more than half of the total amount of time within any of the CPMG sequences actually takes place between individual RF pulses, rather than during actual transmission of RF power.

Several methods are known in the art for dealing with the problem of non-transmitting time in an NMR measurement set. The first method assumes a known, fixed relationship between $T_1$ and $T_2$, as suggested for example, in *Processing of Data from an NMR Logging Tool*, R. Freedman et al, Society of Petroleum Engineers paper no. 30560 (1995). Based on the assumption of a fixed relationship between $T_1$ and $T_2$, the waiting (repolarization) time between individual CPMG measurement sequences is shortened and the measurement results are adjusted using the values of $T_2$ measured during the CPMG sequences. Disadvantages of this method are described, for example in, *Selection of Optimal Acquisition Parameters for MRIL Logs*, R. Akkurt et al, The Log Analyst, vol. 36, no. 6, pp. 43–52 (1996). These disadvantages can be summarized as follows. First, the relationship between $T_1$ and $T_2$ is not a fixed one, and in fact can vary over a wide range, making any adjustment to the purported $T_1$ measurement based on the $T_2$ measurements inaccurate at best. Second, in porous media $T_1$ and $T_2$ are distributions rather than single values. It has proven difficult to "adjust" $T_1$ distributions based on distributions of $T_2$ values.

U.S. Pat. No. 6,049,205 to Taicher et al having the same assignee as the present application and the contents of which are fully incorporated herein by reference, teaches a method for determination of $T_1$ and $T_2$. The static magnetic field in the disclosed device has a field gradient, so that an RF pulse of a selected frequency excites nuclei in a specific portion of the formation determined by the gyromagnetic ratio. By altering the frequency of excitation, different regions of the formation may be analyzed. U.S. Pat. No. 5,936,405 to Prammer et al teaches making interleaved measurements at different frequencies to obtain, in a single logging pass, multiple data streams corresponding to different recovery times and/or diffusivity for the same spot in the formation. The resultant data streams are processed to determine mineralogy-independent water and hydrocarbon saturations and porosity estimates.

In order for these multiple frequency measurements to be made efficiently, it is important that there be no interference between echo signals produced by the RF pulse sequences associated with the different frequencies of acquisition. As noted above, the bandwidth of the tipping pulse used in a CPMG sequence is greater than the bandwidth of the refocusing pulses. As a result of this, there is a possibility that a refocusing pulse associated with one of he CPMG sequences and having one RF frequency may have a sensitive zone in the formation that is affected by a tipping pulse of one of the other CPMG sequences. The interference between the wave trains can lead to erroneous results. To reduce interference between trains measured at neighboring frequencies $f_1$ and $f_2$, the separation between the frequencies has to be as large as possible. On the other hand, the electronics required for the wider separation is harder to build and the resulting pulse sequence is inefficient. It is desirable to have a method for multiple frequency NMR measurements that is relatively easy to apply and does not lead to a significant increase in the inefficiency of the logging. The present invention satisfies this need.

SUMMARY OF THE INVENTION

The present invention is a method for reducing the interference between echo trains of multiple frequency NMR logging applications using a gradient logging tool. The reduction in interference is obtained by shaping the envelope of the tipping pulse so that its bandwidth is reduced relative to a rectangular pulse producing substantially the same rotation of nuclear spins. The major contribution to the interference between different logging sequences comes from the sidelobes in the spectra of the excitation signal caused by modulating the RF signal with a square wave. In the present invention, by shaping the tipping pulse, the interference is greatly reduced. In an alternate embodiment of the invention, the refocusing pulses are also shaped.

DESCRIPTION OF THE PREFERRED EMBODIMENT

An NMR well logging apparatus which is suitable for use with this invention is described, for example, in U.S. Pat. No. 5,712,566 to Taicher et al., the contents of which are fully incorporated herein by reference. The apparatus described therein includes a magnet for inducing a static magnetic field in the earth formations. The static magnetic field includes an amplitude gradient directed radially inwardly towards the longitudinal axis of the instrument. The apparatus disclosed in the Taicher '566 patent includes an antenna through which pulses of RF power are conducted to excite nuclei of the earth formations surrounding the instrument. The antenna includes a wire coil wound around a high magnetic permeability ferrite. The ferrite includes a frequency control coil wound thereon. By passing a selectively controllable DC voltage through the frequency control coil, the tuning frequency of the antenna can be selectively controlled, making transmission and reception of RF energy at different frequencies possible. Since the static magnetic field imparted by the magnet disclosed in the Taicher '566 patent includes an amplitude gradient, conducting NMR measurements at different frequencies will result in these different frequency NMR measurements taking place in different sensitive (excitation) volumes.

It is to be clearly understood that the apparatus disclosed in the Taicher '566 patent application is not the only apparatus which can be used for this invention. For purposes of this invention it is only necessary that the NMR apparatus be able to selectively excite different sensitive volumes to nuclear magnetic resonance, and selectively receive NMR signals from each of the selectively excited sensitive volumes. Using multiple frequencies for individual NMR measurement sequences in a gradient static magnetic field is a particularly convenient means by which to carry out the method of this invention, and so the apparatus disclosed in the Taicher '566 patent is a particularly convenient instrument, but not the exclusive instrument by which to carry out the method of this invention.

Figure 1:
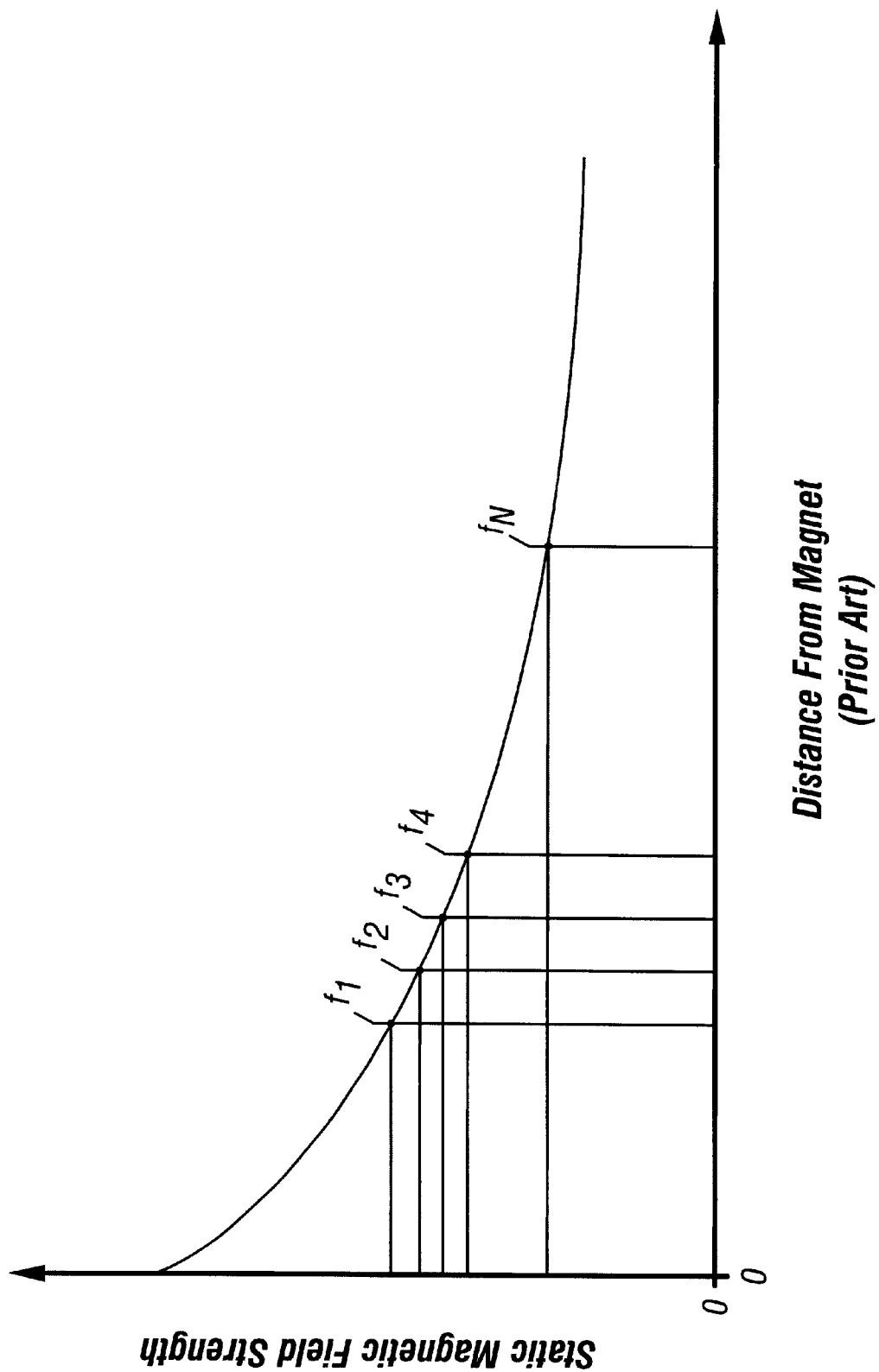
FIG. 1 (PRIOR ART) shows an example of a gradient magnetic field in an NMR device.

FIG. 1 shows a graph of the amplitude of the static magnetic field, with respect to distance from the magnet, for the well logging apparatus described in the Taicher '566 patent. The amplitude of the static magnetic field generally decreases with respect to the lateral distance from the magnet. As is well known in the art, nuclear magnetic resonance conditions occur when a radio frequency magnetic field is applied to materials polarized along a static magnetic field where the frequency of the RF magnetic field matches the product of the static magnetic field strength and the gyromagnetic ratio of the nuclei being polarized by the static magnetic field, this product being referred to as the Larmor frequency. As can be inferred from the graph in FIG. 1, by adjusting the frequency of the RF magnetic field, the distance from the magnet at which nuclear magnetic resonance conditions occur can be changed corresponding to the static magnetic field amplitude at that particular distance from the magnet. For example, if frequency $f_1$ is the highest frequency, resonance will occur at the smallest distance to the magnet, and so on through lower frequencies $f_2$ through $f_n$. Because nuclear magnetic resonance only occurs where the static magnetic field strength matches the RF magnetic field frequency, nuclear magnetic resonance measurements can be conducted within a number of different non-overlapping sensitive volumes by inducing nuclear magnetic resonance at different frequencies. A particular set of non-overlapping sensitive volumes which would result when using the apparatus described in the Taicher '566 patent, for example, would comprise thin annular cylinders each having an average radius corresponding to the particular static magnetic field amplitude in which nuclear magnetic resonance would occur at a particular RF magnetic field frequency. The thickness of each annular cylinder would be related to the bandwidth of a receiver circuit in the NMR instrument and the rate at which the static magnetic field changes in amplitude.

U.S. Pat. No. 6,049,205 to Taicher et al, the contents of which are fully incorporated herein by reference, teaches the use of initial phase alternated pair sequence (PAPS) CPMG sequence for a first frequency $f_1$. As noted above, this frequency $f_1$ corresponds to an initial volume of examination. The initial PAPS sequence is followed by a series of additional PAPS measurement sequences. These additional PAPS measurement sequences are used to excite nuclear magnetic resonance within a number, J, of additional sensitive volumes using a set of J+1 individual operating frequencies, each of which corresponds to one of J+1 static magnetic field amplitudes located within in J+1 different spatial volumes within the earth formation.

Another example of multiple frequency NMR logging is taught by U.S. Pat. No. 5,491,727 to Petit. The Petit patent teaches the use of two interleaved sets of CPMG sequences, each having a different RF frequency and hence a different region of examination.

The examples cited herein of the Taicher '205 patent and the Petit patent are not intended to be limitations and the present invention may be used with any NMR pulse sequence wherein different RF frequency pulses are used wherein there is a possibility of interference between the different pulse sequences.

Figure 2:
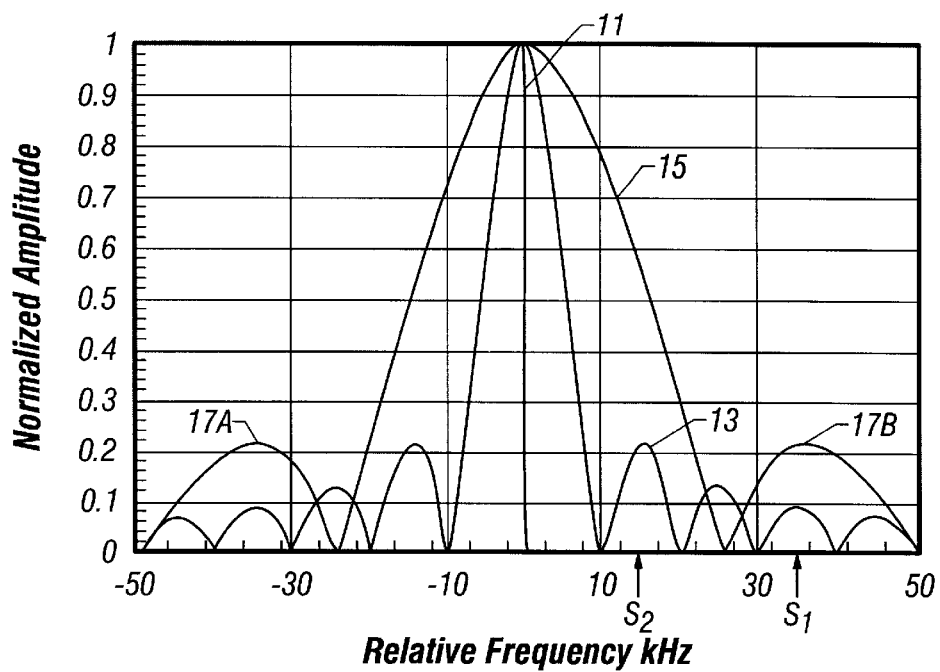
FIG. 2 shows the normalized frequency spectra corresponding to rectangular pulses of different duration.

The frequency spectrum of a monochromatic carrier modulated by a square pulse is given by the well known sync function:

$$F(x) = \frac{2}{\tau} \int_0^{\tau/2} \cos(2\pi x t) \cdot dt = \frac{\sin(\pi x \tau)}{\pi x \tau} \quad (3)$$

where x is the frequency relative to the frequency of the carrier and $\tau$ is the duration of the pulse. The problem with the multiple frequency NMR logging may be understood by reference to FIG. 2. Shown as the single line 11 in FIG. 2 is the frequency spectrum of an unmodulated RF carrier signal, i.e., an infinitely long monochromatic signal. For convenience, the frequency is plotted as a relative frequency with respect to the frequency of the carrier. When this same RF signal is modulated by a square pulse having a duration $\tau$ of 40 μs, the spectrum of the resultant signal is denoted by 15. When this same RF carrier is modulated by a square pulse having a duration $\tau$ of 100 μs, the spectrum of the resultant signal is denoted by 13.

It may be seen in FIG. 2 that when the RF carrier signal is modulated by a square pulse of 40 μs duration, a typical value of the tipping pulses used in NMR logging, the spectrum has significant sidelobes 17a and 17b shifted approximately 35 kHz with respect to the carrier frequency. The significance of this is best appreciated by referring to FIG. 3.

Figure 3:
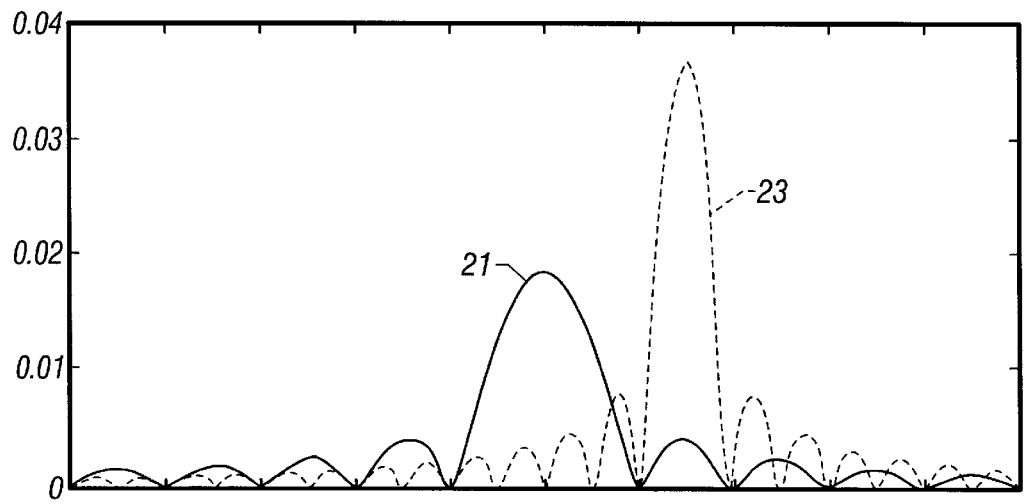
FIG. 3 shows an interference between a tipping pulse at one frequency and a refocusing pulse at an adjacent frequency in prior art multi-frequency NMR acquisition.

The abscissa in FIG. 3 is frequency and the ordinate is the amplitude. Shown is the spectrum 21 of a rectangular tipping pulse for a first region of examination. This is shown with a zero relative frequency, i.e., at a first carrier frequency. Also shown is the spectrum 23 of a rectangular refocusing pulse for a second region of examination with a carrier frequency shifted 30 kHz relative to the first carrier frequency. Two types of interference may be noted in FIG. 3. First, the sidelobes of the refocusing pulse 23 have a sizeable magnitude relative to the main lobe of the first tipping pulse 21. Secondly, the sidelobes of the tipping pulse 21 are large relative to the main lobe of the refocusing pulse 23. What this means is that in a multifrequency NMR logging experiment, if rectangular tipping and refocusing pulses are used, the echo train for any single frequency measurement will have a sizeable interference from signals at adjacent frequencies.

Figure 4:
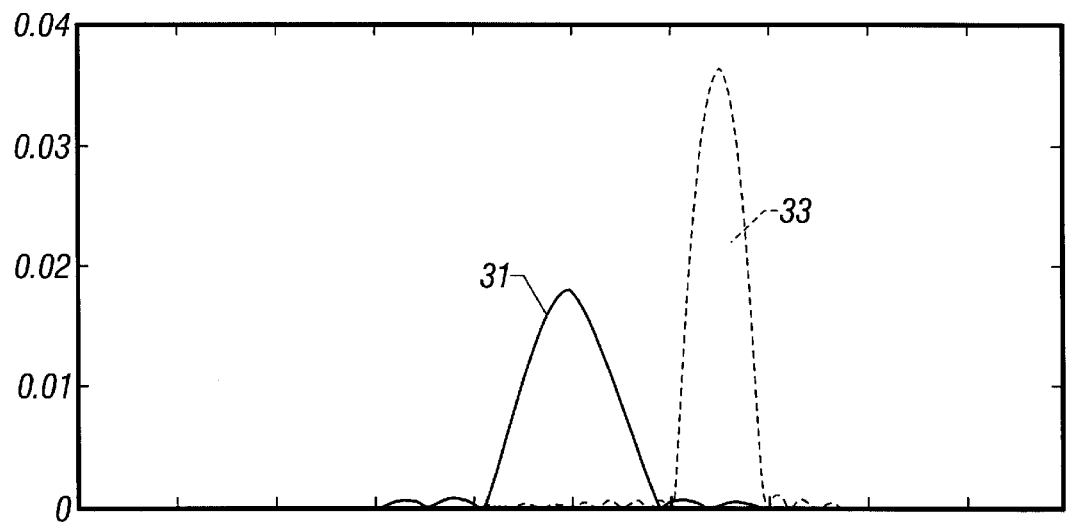
FIG. 4 shows the reduction in interference for the pulses of FIG. 3 by shaping the tipping and refocusing pulses.

FIG. 4 shows similar spectral plots when the first tipping pulse 31 and the refocusing pulse for the second frequency 33 are suitably shaped. The interference between data acquired at different frequencies is substantially zero.

When pulse shaping is used in NMR data acquisition, the rotation angle of the shaped and unshaped pulse should be substantially the same at the carrier frequency. This means that the area under the envelope of a shaped pulse must be the same as the area under the envelope of the corresponding rectangular pulse. This can be achieved in one of two ways or a combination thereof. One option is to keep the peak amplitude constant and increase the overall length of the pulse. Alternatively, the overall length of the pulse is maintained unchanged and the peak amplitude is increased.

Increasing the pulse length is acceptable in the tipping pulse as it is removed in time from the pulse echo signals. Increasing the pulse length of the refocusing pulse is a disadvantage because it leads to an increase in the minimum interecho time $\tau$ in eq. 2. Increasing the pulse length also leads to a reduced bandwidth: this too is acceptable in the tipping pulse as it has a larger bandwidth than the refocusing pulse; it is a disadvantage with refocusing pulses as it leads to a reduction in signal-to-noise ratio.

Increasing the pulse peak amplitude is usually not practical because the peak amplitude is limited by the capability of the electronics hardware. If it were possible it would increase the power consumption per pulse. This is acceptable in the tipping pulses because they form a relatively small portion of the NMR data acquisition. Increasing the pulse peak amplitude is a disadvantage for the refocusing pulses as they represent most of the power consumption, leading to an increase in the power requirements downhole.

Figure 5:
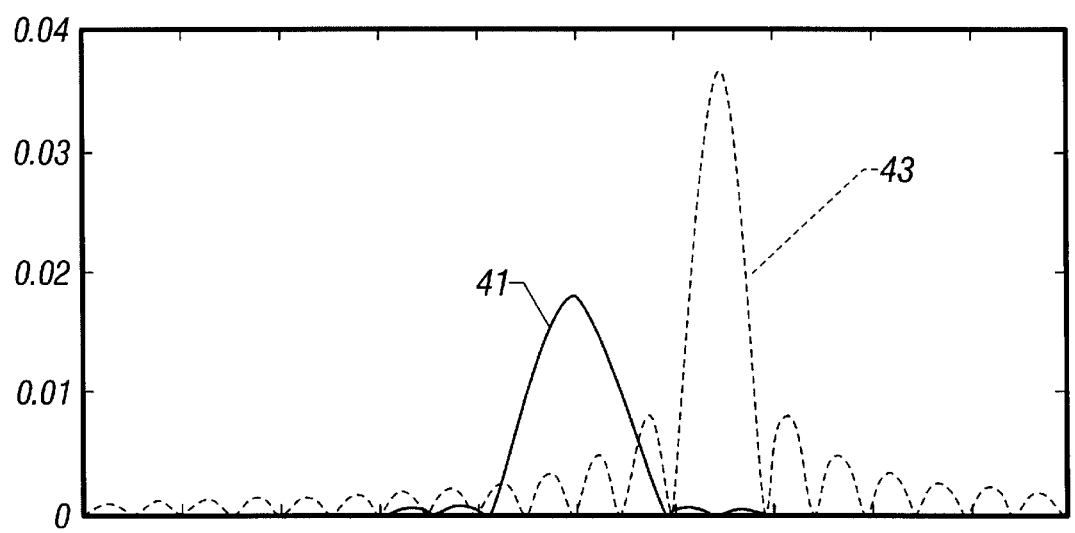
FIG. 5 shows the reduction in interference for the pulses of FIG. 3 by shaping the tipping pulse only.

For the reasons discussed above, in a preferred embodiment of the invention, only the tipping pulse is shaped and the refocusing pulses are not shaped. FIG. 5 shows spectra similar to FIGS. 3 and 4 but with only the tipping pulse 41 being shaped and the refocusing pulse 43 being rectangular. It may be seen that the interference between the sidelobes of the tipping pulse at first carrier frequency and the main lobe of the adjacent refocusing pulse is the same as in FIG. 4. This is important because this interference is what determines the signal-to-noise ratio of the pulse echo sequence at the adjacent frequency. Furthermore, by shaping the tipping pulse and not the refocusing pulse, there is no increase in the int%recho, spacing T and little increase in logging time requirements.

The problem of interference between signals having carriers with proximate frequencies is well studied in communication theory. For example, U.S. Pat. No. 5,491,727 to Petit discloses the use of complicated electronic circuitry for pulse shaping to achieve a minimum interference. The Petit patent teaches a method of optimal pulse shaping wherein there is no sidelobe energy in the frequency domain, or alternatively, no sidelobes in the time domain and minimal sidelobe energy in the frequency domain. The results in Petit suggest that a trapezoidal pulse shape in time would achieve the necessary results. Chebyshev functions are commonly used for pulse shaping in communications systems to reduce interference. Such shaping functions require complicated circuitry to implement.

Figure 6:
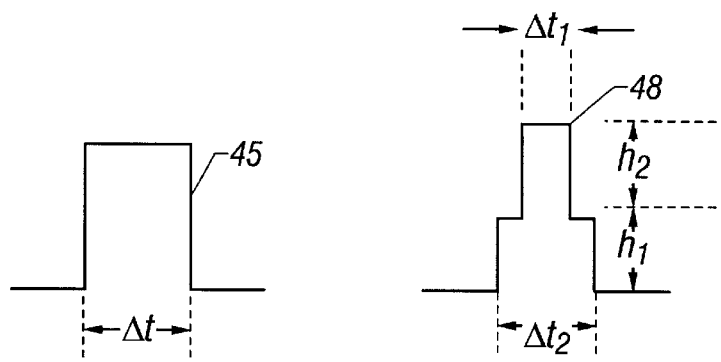
FIG. 6 shows an example of a simple shaping of the tipping pulse.

In one embodiment of the invention, a very simple modification of the tipping pulse has been found to be quite satisfactory. This is best understood by reference to FIG. 6. On the left is shown a prior art rectangular pulse 45 used in NMR logging for shaping both the tipping pulse and the refocusing pulse. On the right is shown a simple shaped pulse 48 that may be considered to be made up of two rectangular pulses, one having a duration $\Delta t_1$ and the other having a duration $\Delta t_2$. Such a pulse may be denoted as $$g(t)=h_1(\Delta t_1)+h_2(\Delta t_2) \tag{4}$$

Figure 7:
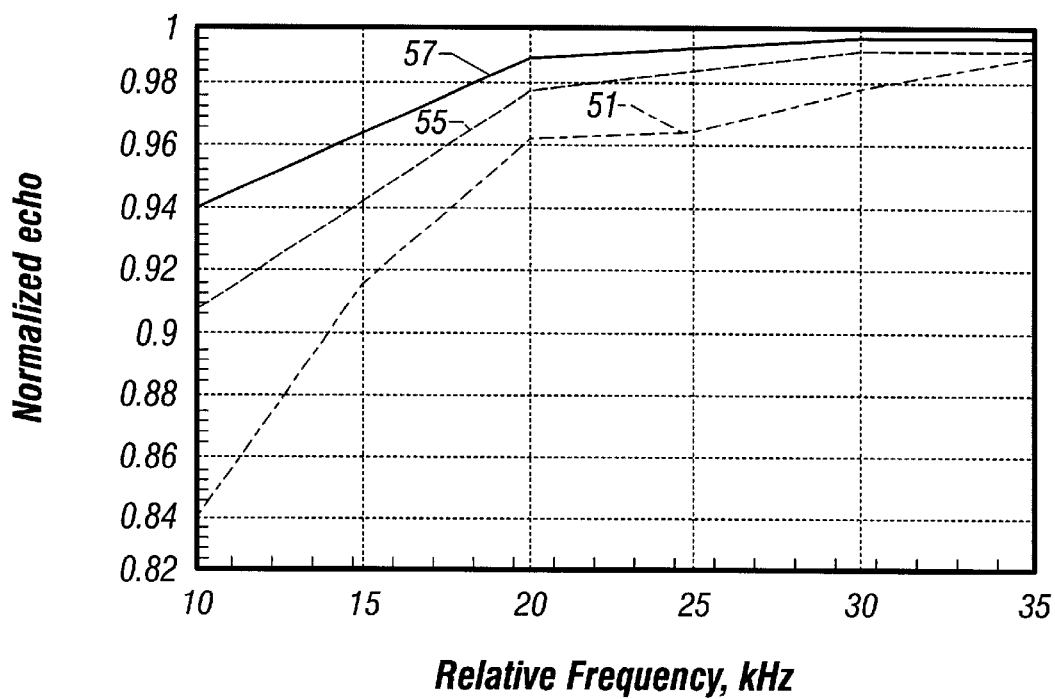
FIG. 7 shows the reduction in interference between adjacent multifrequency CPMG echo trains using the pulse shaping of the present invention

FIG. 7 shows simulation results of including shaped pulses, in NMR data acquisition. The modified CPMG sequence according to the present invention may be represented as $$TW-s_190_x(\tau-180_y-\tau-echo)_j \tag{5}$$

where TW is a wait time, $\tau$ is the Carr-Purcell timing, and $s_190_x$ is a shaped tipping pulse and $180_y$ is a refocusing pulse. The subscripts x and y denote phase shifts of 0 and $\tau/2$ of the corresponding pulses with reference to a phase of the RF carrier signal. The need for these phase shifts would be known to those versed in the art. In an alternate embodiment of the invention, the refocusing pulses may also be shaped.

FIG. 7 shows examples of simulation results when the shaped pulse $s_1$ has the form $g_1$ given by Eq. (4). Similar results are obtained for other shaping pulses but are not shown here.

The curves in FIG. 7 all correspond to an effective duration of 100 $\mu$s for the refocusing pulse. The abscissa is the frequency separation between sequential echo trains and the ordinate is the normalized amplitude of the third echo of the corresponding echo trains. The third echo is selected because the first and second echos are usually dominated by the ring-down signal from the transmitter excitation.

The curve 51 corresponds to rectangular tipping and refocusing pulses of 50 $\mu$s and 100 $\mu$s respectively and shows a more than 3.5% (amplitude less than 0.97) in the amplitude for a frequency separation of 20 kHz. Turning next to 57, this corresponds to the case where both the tipping and refocusing pulses are shaped using a shaping pulse of the type given by eq. 4. For such shaped pulses, the drop in echo amplitude for a 20 kHz separation is approximately 1.0%. Finally, the curve 55 is obtained when only the tipping pulse is shaped (according to Eq. 4) and the refocusing pulse is a hard rectangular pulse. It may also be noted from FIG. 5 that shaping the tipping pulse only (curve 55) results in less than 2% interference at a frequency separation of 20 kHz. This illustrates that shaping the tipping pulse alone give much of the benefit of shaping both the tipping and refocusing pulses.

While the foregoing disclosure is directed to the preferred embodiments of the invention, various modifications will be apparent to those skilled in the art. It is intended that all variations within the scope and spirit of the appended claims be embraced by the foregoing disclosure.

What is claimed is:

1. A method of making nuclear magnetic resonance measurements of an earth formation using a multifrequency gradient logging tool conveyed therein, the method comprising:

(a) magnetically polarizing nuclei in said earth formation with a static magnetic field having a gradient therein;

(b) acquiring a first echo train in a first sensitive volume of the earth formation for determining a parameter thereof, said first echo train produced by a first pulse sequence comprising a first RF frequency, a first shaped tipping pulse and a first plurality of refocusing pulses at said first RF frequency; and (c) acquiring a second echo train corresponding to a second sensitive volume of the earth formation different from the first sensitive volume for determining a parameter thereof, said second echo train produced by a second pulse sequence comprising a second RF frequency, a second RF tipping pulse and a second plurality of refocusing pulses at said second RF frequency;

wherein a shape of said first tipping pulse is selected to reduce an interference (overlap in the frequency domain) between said first tipping pulse and a refocusing pulse of said second pulse sequence and a resulting disturbance of magnetization in said second sensitive volume by said fist pulse sequence.

2. The method of claim 1 wherein the second tipping pulse is a shaped pulse.

3. The method of claim 1 wherein the first tipping pulse has, in the frequency domain, smaller sidelobes than sidelobes associated with a rectangular pulse producing a rotation of nuclear spins substantially the same as a rotation produced by the first shaped tipping pulse.

4. The method of claim 2 wherein the first and second shaped tipping pulses have, in the frequency domain, smaller sidelobes than sidelobes associated with a first rectangular pulse and a second rectangular pulse producing substantially the same rotation of nuclear spins in said earth formation as said first and second shaped tipping pulse respectively.

5. The method of claim 1 wherein the first tipping pulse comprises a composite pulse comprising a first retangular pulse and a second rectangular pulse, said first and second rectangular pulses each having a duration and an amplitude.

6. The method of claim 5 wherein the amplitudes of the first and second rectangular pulses are substantially equal.

7. The method of claim 5 wherein the duration of the first rectangular pulse is greater than the duration of the second rectangular pulse.

8. The method of claim 1 wherein the first plurality of refocusing pulses is selected from the group consisting of (i) rectangular pulses (ii) composite pulses, and, (iii) shaped pulses.

9. The method of claim 1 wherein the first RF frequency differs from the second RE frequency by less than 40 kHz.

10. The method of claim 1 wherein the frequency spectrum of the first tipping pulse is substantially described by a Chebyshev function.

11. The method of claim 1 wherein at least one of the first plurality of refocusing pulses comprises a rectangular pulse.

12. The method of claim 1 wherein at least one of the second plurality of refocusing pulses comprises a rectangular pulse.

13. The method of claim 2 wherein at least one of the first plurality of refocusing pulses comprises a rectangular pulse.

14. The method of claim 2 wherein at least one of the second plurality of refocusing pulses comprises a rectangular pulse.

15. The method of claim 1 wherein the first plurality of refocusing pulses has a substantially constant tipping angle.

16. The method of claim 2 wherein the second plurality of refocusing pulses has a substantially constant tipping angle.

17. The method of claim 1 wherein an overlap in the frequency domain between the first shaped tipping pulse and the second tipping pulse is reduced relative to an overlap between the second tipping pulse and a rectangular tipping pulse at said first frequency having the same tip angle as the first shaped tipping pulse.

* * * * *